United States Patent
Popa et al.

(10) Patent No.: US 8,945,228 B2
(45) Date of Patent: Feb. 3, 2015

(54) ENDPLATE FOR A VERTEBRAL IMPLANT

(71) Applicant: Depuy Synthes Products, LLC, Raynham, MA (US)

(72) Inventors: Samantha Popa, Columbus, OH (US); Roman Randegger, Oberdorf (CH); Felix Aschmann, Oberdorf (CH); Joern Richter, Kandern (DE)

(73) Assignee: Depuy Synthes Products, LLC, Raynham, MA (US)

( * ) Notice: Subject to any disclaimer, the term of this patent is extended or adjusted under 35 U.S.C. 154(b) by 167 days.

(21) Appl. No.: 13/678,152

(22) Filed: Nov. 15, 2012

(65) Prior Publication Data

US 2014/0135931 A1 May 15, 2014

(51) Int. Cl.
*A61F 2/44* (2006.01)
*A61F 2/30* (2006.01)

(52) U.S. Cl.
CPC .............. *A61F 2/44* (2013.01); *A61F 2/30739* (2013.01); *A61F 2002/30362* (2013.01); *A61F 2002/30378* (2013.01); *A61F 2002/30387* (2013.01); *A61F 2002/30538* (2013.01); *A61F 2002/30571* (2013.01); *A61F 2002/30594* (2013.01)
USPC ..................................... 623/17.16

(58) Field of Classification Search
USPC ........................................... 623/17.11–17.16
See application file for complete search history.

(56) References Cited

U.S. PATENT DOCUMENTS

| 4,932,975 | A | 6/1990 | Main et al. |
|---|---|---|---|
| 5,534,029 | A | 7/1996 | Shima |
| 5,827,328 | A | 10/1998 | Buttermann |
| 5,895,428 | A | 4/1999 | Berry |
| 6,743,257 | B2 | 6/2004 | Castro |
| 6,808,538 | B2 | 10/2004 | Paponneau |
| 7,153,325 | B2 | 12/2006 | Kim et al. |
| 7,235,101 | B2 | 6/2007 | Berry et al. |
| 7,255,714 | B2 | 8/2007 | Malek |
| 7,402,176 | B2 | 7/2008 | Malek |
| 7,458,988 | B2 | 12/2008 | Trieu et al. |
| 7,563,284 | B2 | 7/2009 | Coppes et al. |
| 7,819,922 | B2 | 10/2010 | Sweeney |
| 7,828,846 | B2 | 11/2010 | Biedermann et al. |
| 8,016,886 | B2 | 9/2011 | Albert et al. |
| 8,021,424 | B2 | 9/2011 | Beger et al. |
| 2005/0085910 | A1 | 4/2005 | Sweeney |

(Continued)

FOREIGN PATENT DOCUMENTS

| DE | 41 09 941 | 10/1992 |
|---|---|---|
| DE | 20 2008 001 079 | 3/2008 |

(Continued)

OTHER PUBLICATIONS

International Search Report and Written Opinion (PCT/US2012/065287); Aug. 22, 2013.

*Primary Examiner* — Sameh Boles
(74) *Attorney, Agent, or Firm* — Dunlap Codding, P.C.

(57) ABSTRACT

An endplate for a vertebral implant comprises a base portion connectable to one end of a support body and a bone contact portion. The bone contact portion including a plurality of bone contact sections, each of which has a bone contact surface and extends from the base portion in such a way that each of the bone contact sections is deflectable relative to the base portion independently of an adjacent one of the bone contact sections when a compressive load is applied to the bone contact surfaces of the bone contact sections.

6 Claims, 7 Drawing Sheets

(56) References Cited

U.S. PATENT DOCUMENTS

| | | |
|---|---|---|
| 2005/0113924 A1 | 5/2005 | Buttermann |
| 2005/0283241 A1 | 12/2005 | Keller et al. |
| 2006/0064167 A1 | 3/2006 | Keller |
| 2006/0064168 A1 | 3/2006 | Keller |
| 2006/0200241 A1 | 9/2006 | Rothman et al. |
| 2006/0293755 A1 | 12/2006 | Lindner et al. |
| 2007/0050030 A1 | 3/2007 | Kim |
| 2007/0123990 A1 | 5/2007 | Sharifi-Mehr |
| 2007/0129806 A1 | 6/2007 | Harms et al. |
| 2007/0250173 A1 | 10/2007 | Berry et al. |
| 2008/0015704 A1 | 1/2008 | Gradl et al. |
| 2008/0065211 A1 | 3/2008 | Albert et al. |
| 2008/0172129 A1 | 7/2008 | Kim et al. |
| 2009/0105835 A1 | 4/2009 | Hovda et al. |
| 2010/0016969 A1 * | 1/2010 | Richter et al. ............ 623/17.11 |
| 2010/0152856 A1 | 6/2010 | Overes et al. |

FOREIGN PATENT DOCUMENTS

| | | |
|---|---|---|
| EP | 1 290 993 | 3/2003 |
| EP | 1 459 710 | 9/2004 |
| EP | 1 212 992 | 8/2007 |
| WO | 2006/054111 | 5/2006 |
| WO | 2008/106912 | 9/2008 |

* cited by examiner

ENDPLATE FOR A VERTEBRAL IMPLANT

BACKGROUND

1. Field of the Inventive Concepts

The inventive concepts disclosed herein are generally directed to medical implants, and more particularly, but not by way of limitation, to an endplate for vertebral implants and to methods of using same.

2. Brief Description of Related Art

The human spinal column, or spine, is highly complex, in that it includes over twenty bones coupled to one another so as to support the body and to house and protect critical elements of the nervous system. In addition, the spine is a highly flexible structure, capable of bending and twisting in multiple directions. The bones and connective tissues of an adult human spine are coupled sequentially to one another by a tri joint complex which consists of an anterior joint between vertebral bodies, and two posterior facet joints. The vertebral bodies of adjacent vertebrae are separated and cushioned by cartilage spacers referred to as intervertebral discs. The vertebral bones of the spine are classified as cervical, thoracic, lumbar, and sacral. The cervical portion of the spine, which includes the upper portion of the spine up to the base of the skull, is the most flexible of all the regions of the spinal column, and includes the first seven vertebrae. The twelve intermediate bones comprise the thoracic vertebrae, and connect to the lower spine which comprises the five lumbar vertebrae. The base of the spine includes the sacral bones (including the coccyx).

A typical human thoracic and lumbar vertebra consists of two essential parts: an anterior (front) segment, which is the vertebral body; and a posterior (back) segment, which is the vertebral arch. The vertebral arch is formed by a pair of pedicles and a pair of laminae, and supports seven processes—four articular, two transverse, and one spinous.

The vertebral body is the largest portion of the vertebrae and is generally cylindrical in shape. Vertebral bodies have upper and lower surfaces, which are generally flat or slightly concave. The surfaces are roughened to allow for the attachment of the intervertebral discs. The vertebral bodies and the intervertebral discs cooperate to provide structural support to the spinal column, with the intervertebral discs cushioning the vertebrae and absorbing and adapting to forces exerted on the vertebral bodies.

In some cases of spinal injuries, the forces exerted on the spinal column are so great, as to cause a partial or complete fracture of one or more of the vertebral bodies, and significant damage to the intervertebral discs surrounding the fractured vertebrae. A vertebral fracture or collapse may also be caused by osteoporosis, infection, tumors, or other diseases.

Regardless of the cause, it is difficult for the damaged vertebral body and intervertebral discs to heal due to the constant forces exerted on the spinal column, or due to the disease progression. Further, due to bulging or displaced damaged vertebrae or intervertebral discs, pressure may be exerted on the spinal cord, or other neural tissues surrounding the damaged vertebrae or intervertebral discs, which may lead to significant pain, neurological damage, and even paralysis in some severe cases.

Surgical procedures called interbody fusion (IBF) and vertebral body replacement (VBR) have been developed to remove the damaged intervertebral discs in the case of IBF and the damaged vertebral body and intervertebral discs in the case if VBR, and to replace them with an implant, such that the height, alignment, and curvature of the spinal column is maintained or is not significantly compromised.

By way of example, VBR is generally performed by locating the damaged vertebral body (e.g., with medical imaging) and accessing it via an appropriate surgical incision. Once the vertebral body is accessible, surgical tools may be used to remove a portion or all of the vertebral body and the two intervertebral discs surrounding the removed vertebral body, such that the lower surface of the vertebral body above and the upper surface of the vertebral body below the removed vertebral body are exposed.

Next, a generally cylindrical implant of appropriate size is selected and inserted in the location of the removed vertebral body. The implant generally has endplates, or another interface, which contact the exposed lower surface of the vertebral body above the removed vertebral body, and the exposed upper surface of the vertebral body below the removed vertebral body. The endplates are configured to engage the implant with the two adjacent vertebral bodies and to keep it in place once implanted.

Some existing VBR implants allow surgeons to adjust the height of the implant to match the original height, alignment, or curvature of the patient's spine, and some implants have a porous hollow body, which allows surgeons to insert a bone graft into the implant. The bone graft may eventually grow through, or around, the implant, and may fuse the two vertebrae that are in contact with the implant over time. One or more supplemental fixation devices, such as stabilizing rods, plates, or bone screws, may be attached to the vertebrae above and below the implant, or even to the implant itself, to provide additional stabilization of the spine while the bone graft is fusing the two vertebrae together. If the VBR implant is a bone-fusion implant, over the next several months the bone graft grows into, or around, the implant to eventually fuse the adjacent vertebral bodies together. If the VBR implant is a non-fusion implant, the supplemental fixation devices and the VBR implant may function to replace the removed vertebral body and discs, and the VBR implant and adjacent vertebrae may not be fused together.

IBF is performed in a manner generally similar to VBR except that only an intervertebral disc is removed such that the lower surface of the vertebral body above and the upper surface of the vertebral body below the removed intervertebral disc are exposed. Next, one or more implants of appropriate size are selected and inserted in the space of the removed disc.

The design, shape, and angle of the vertebral implant endplates that contact the adjacent vertebrae are important in ensuring proper spinal height, alignment, and curvature, and in securely attaching the vertebral implant to adjacent vertebrae, such that the implant does not become dislodged, or otherwise displaced post-implantation.

However, existing vertebral implant endplates suffer from several disadvantages. For example, existing vertebral implant endplates have bone contact surface designs which, due to local patient anatomies and angulations, may result in concentrating a large amount of force onto a small area on the prior art endplate bone contact surface. This is referred to as point-loading and may significantly increase the chances of adjacent vertebral body subsidence.

Further, existing vertebral implant endplates generally have a fixed angle relative to the implant body, and typically kits with several fixed-angle endplates are supplied to surgeons. Surgeons determine the appropriate combination of fixed-angle endplates according to patient anatomy during the procedure, which involves inserting a vertebral implant with a selected combination of endplates and taking an image of the spine. Inter-operative imaging allows the surgeon to verify the optimal spinal height and curvature is restored. If not, the vertebral implant is extracted, a different combination of fixed-angle endplates is selected and implanted with the vertebral implant, and the alignment verification step is repeated. This prolongs the surgical procedure, and in some cases may result in less than perfect match between the available fixed-angle endplates and local patient angulations and anatomy, which may lead to point-loading or may delay bone fusion, for example.

DETAILED DESCRIPTION OF EXEMPLARY EMBODIMENTS

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments, or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having," and any variations thereof, are intended to cover a non-exclusive inclusion. For example, a process, method, article, or apparatus that comprises a list of elements is not necessarily limited to only those elements, and may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments disclosed herein. This is done merely for convenience and to give a general sense of the inventive concepts. This description should be read to include one or at least one and the singular also includes the plural unless it is obvious that it is meant otherwise.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

As is known by persons of ordinary skill in the art, established human anatomical orientation designations are used to avoid ambiguities when referring to a body part relative to another body part. A standard anatomical position (i.e., standing upright facing forward with arms to the side, palms facing forward, thumbs pointing laterally away from the body) has been established, and such orientation designations refer to the various body parts in the standard position, without regard to their actual position. For the purposes of the instant disclosure, such standard human anatomy terminology may be used to describe the various orientation and interrelationships of the different parts of a user's body. For example, the terms "anterior," "posterior," "superior," "inferior," "lateral," "medial" and related terms or phrases may be used to designate relative positions and orientations in the patient's body to which reference is made, and are not meant to be limiting. Further, the terms "left," "right," "lower," "upper," "top," and "bottom" may designate general directions in the drawings to which reference is made, for example, and are not meant to be limiting. The terms "inner," "inwardly," or "distally," and "outer," "outwardly," or "proximally" may refer to directions toward or away from the geometric center of a device and related parts thereof, or a patient's body, for example, and are not intended to be limiting.

As used herein, the term "patient" is not limited to a human being, and is intended to include all organisms, whether alive or dead, including any species having soft tissues and bones. For example, surgical implant endplates according to the instant disclosure may be used in a living human, horse, cow, sheep, cat, dog, and the like. As another example, surgical implant endplates according to the instant disclosure may be used in a non-living organism, or in an artificial anatomical model to train medical or veterinary personnel in surgical techniques. Further, a virtual representation of surgical implant endplates according to the instant disclosure may be used in a virtual simulation to train medical or veterinary personnel in surgical techniques, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 1:
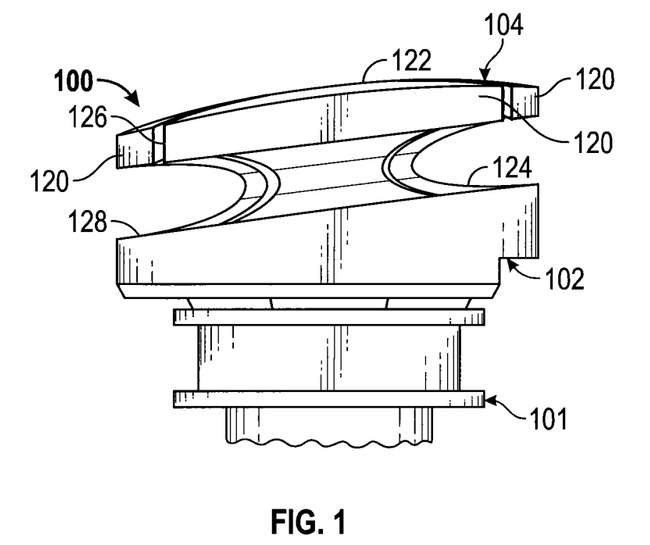
FIG. 1 is an elevational view of an endplate constructed in accordance with the inventive concepts disclosed herein shown connected to a support body.
Figure 2:
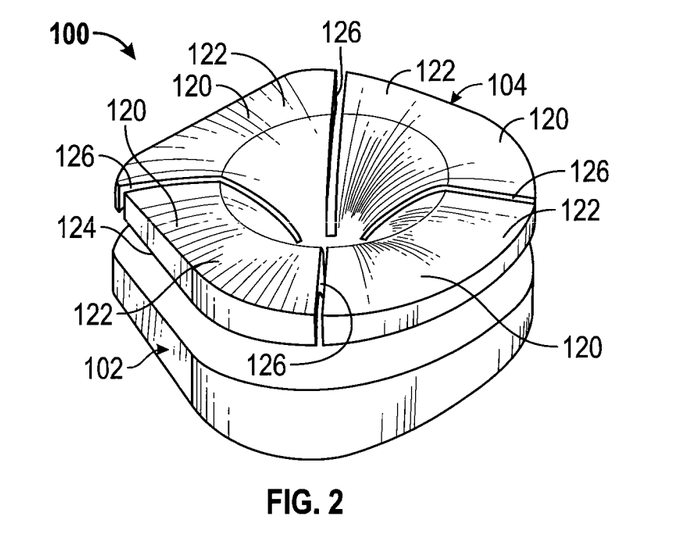
FIG. 2 is a perspective view of the endplate of FIG. 1.

Referring now to drawings, and more particularly to FIG. 1, an exemplary embodiment of an endplate 100 for use in a vertebral implant is shown connected to a portion of a support body 101. As discussed above, vertebral implants are known in the art. Vertebral implants generally include a support body positioned between two endplates selected to best fit the exposed lower surface of the vertebral body above the removed disc, or discs and vertebral body, and the exposed upper surface of the vertebral body below the removed disc or discs and vertebral body, respectively. The support body 101 may be formed in a variety of configurations. For example, some support bodies have a fixed length, while others are adjustable so that the distance between the two endplates is adjustable to allow a surgeon to match the original height, alignment, or curvature of the patient's spine. Also, some support bodies are porous so that bone graft material may be inserted into the support body to promote fusion.

Referring now to FIGS. 1-4, the endplate 100 has a base portion 102 and a bone contact portion 104. The base portion 102 provides a foundation for connecting with the support body 101 and for supporting the bone contact portion 104. The bone contact portion 104 extends from the base portion 102 and is adapted to conform to the contour of the respective surface of a vertebral body with which the endplate 100 is positioned in contact to distribute loads placed on the endplate 100.

Figure 3:
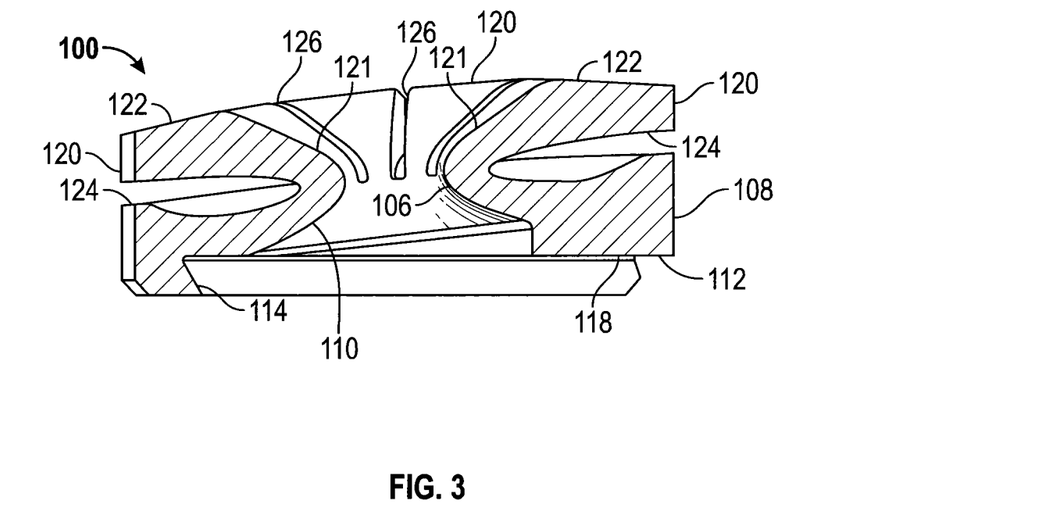
FIG. 3 is a cross-sectional view of the endplate of FIG. 1 shown connected to the support body.
Figure 4:
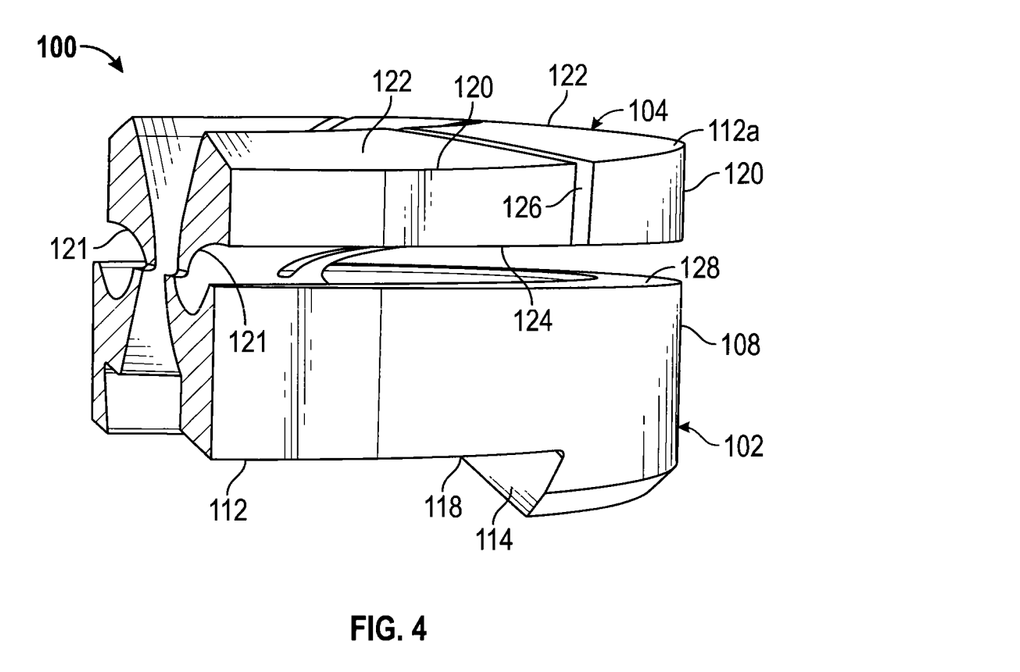
FIG. 4 is a perspective, cross-sectional view of the endplate.
Figure 5:
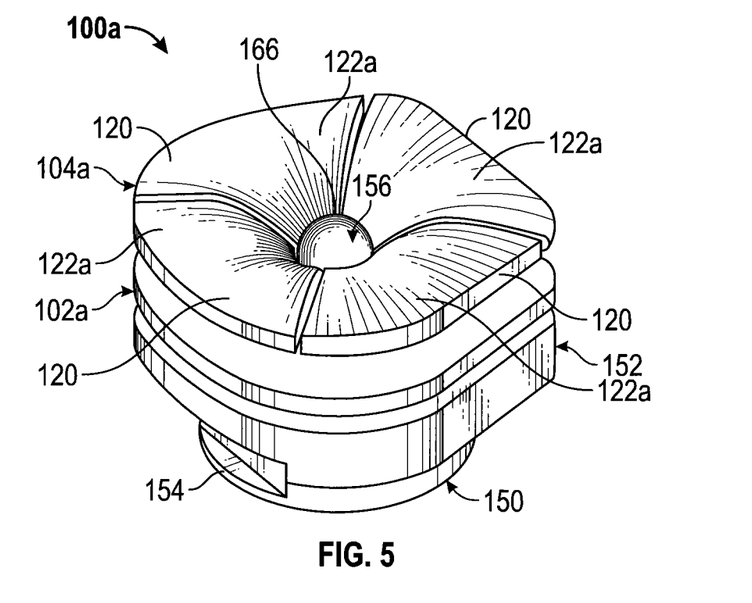
FIG. 5 is a top perspective view of another embodiment of an endplate constructed in accordance with the inventive concepts disclosed herein shown connected to a portion of a support body.
Figure 6:
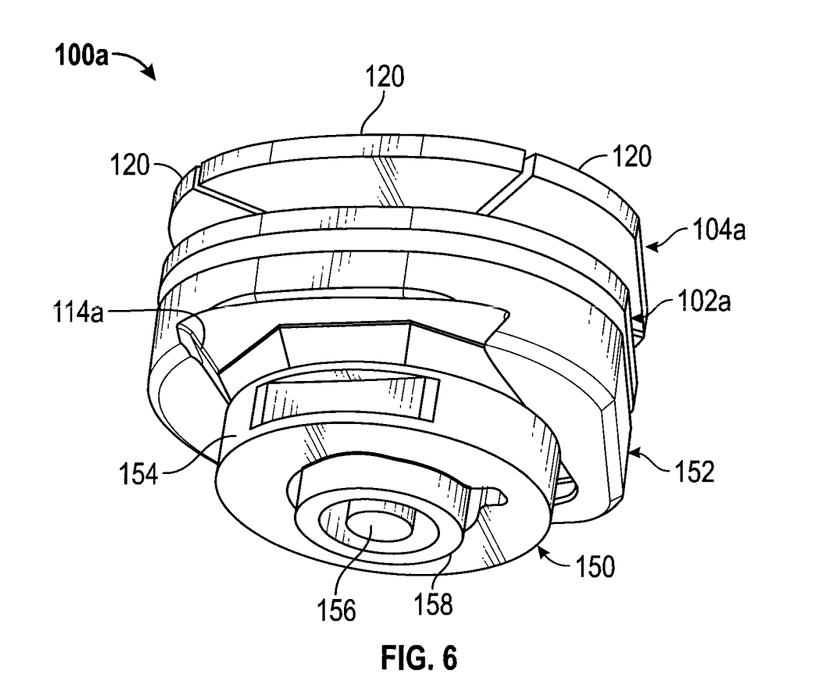
FIG. 6 is a bottom perspective view of the endplate of FIG. 5.
Figure 7:
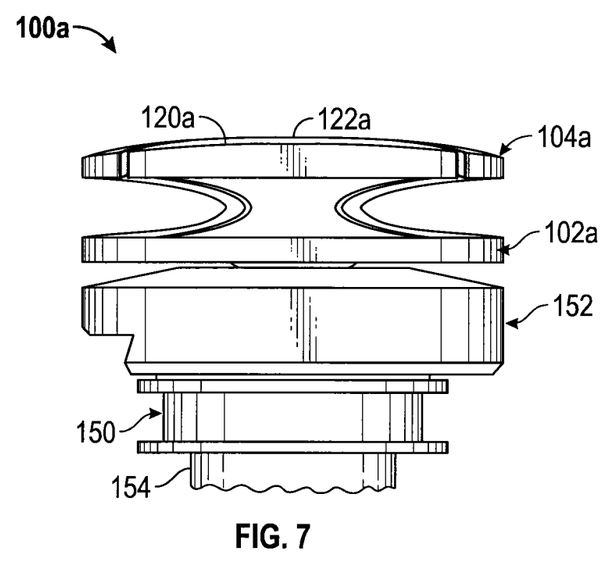
FIG. 7 is an elevational view of the endplate of FIG. 5.
Figure 8:
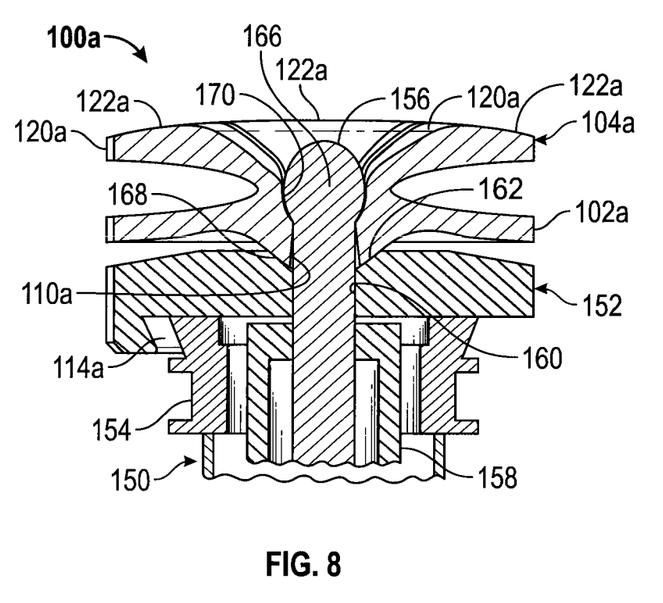
FIG. 8 is a cross-sectional view of the endplate of FIG. 5.

As best illustrated in FIG. 3, the base portion 102 has an inner periphery 106 and an outer periphery 108 with the inner periphery 106 defining a central opening 110. The base portion 102 is adapted to be connected to the support body 101. To this end, the base portion 102 may include a bottom surface 112 provided with a connector 114, e.g., a recess 118, that is configured to receive and retain a corresponding portion of the support body 101. The connector 114 may be formed in a variety of configurations for making connection with the support body 101. For example, the base portion 102 may be attached to the support body 101 by press fit, snap fit, or a threaded connection. Further, in some embodiments, the endplate 100 and the support body 101 may be formed as a unitary body, while in some exemplary embodiments the base portion 102 may be connected to the support body 101 via welds, seams, screws, brackets, bolts, joints, adhesives, and combinations thereof. In some exemplary embodiments of the inventive concepts disclosed herein, the support body 101 may be another bone contact portion 102 such that the vertebral implant includes a base portion 102 and two opposing bone-contacting portions 104.

The bone contact portion 104 includes a plurality of bone contact sections 120 with each of the bone contact sections 120 having a bone contact surface 122. The bone contact sections 120 extend from the base portion 102 in such a way that each of the bone contact sections 120 are sufficiently resilient so that the bone contact surfaces 122 are deflectable relative to the base portion 102 independently of the other the bone contact surfaces 122 when a compressive load is applied to the bone contact surfaces 122 of the bone contact sections 120.

The bone contact sections 120 extend radially upwardly and outwardly from the base portion 102 near the inner periphery 106 thereof with each of the bone contact sections 120 flaring outwardly from a proximal end to a distal end to define the bone contact surfaces 122. Each of the bone contact sections 120 includes a spring portion 121 that is dimensioned so that the bone contact surfaces 122 are resiliently deflectable. It should be appreciated that the spring portions 121 may be formed in a variety of shapes and sizes to affect the flexibility characteristics desired. The bone contact sections 120 are spaced from the adjacent bone contact section 120 along the sides thereof so as to define a slot 126 between each of the contact sections 120. The slots 126 can be formed to have a variety of lengths and widths, but the slots 126 desirably have a width sufficient that the bone contact sections 120 do not interfere with the deflection of the adjacent bone contact sections 120 and the slots 126.

The bone contact sections 120 further extend from the base portion 102 such that the base portion 102 and the bone contact sections 120 of the bone contact portion 104 cooperate to define an annular channel 124. The annular channel 124 provides clearance between a distal end of the bone contact sections 120 and the outer periphery 108 of the base portion 102 to allow the bone contact sections 120 to flex relative to the base portion 102. The distal end of the bone contact sections 120 may be substantially aligned with the outer periphery 108 of the base portion and the annular channel 124 may be sized so that the base portion 102 services as a stop to limit the deflection of the bone contact sections 120. To this end, the base portion 102 may include a planar contact surface 128 near the outer periphery 108 of the base portion 102 that is spaced from the distal ends of the bone contact sections 120 a predetermined distance.

In the exemplary embodiment shown in FIGS. 1-4, the bone contact portion 104 includes four bone contact sections 120 which are of equal size and shape. However, the bone contact portion 104 may be formed to include a variety of different number of bone contact sections, such as two, three, five, six or more. Further, the bone contact sections may be formed where the bone contact sections of the endplate 100 have different shapes and sizes, as well as different degrees of flexibility.

The endplate 100 may be formed to have a variety of shapes and sizes adapted to fit in the intervertebral space between adjacent vertebral bodies at any level of the spine. The endplate 100 may be constructed of any desired bio-inert, bio-absorbable, or bio-active implantable material, or combination of materials, including titanium, titanium alloys, surgical steel, nickel titanium (or nitinol), cobalt chromium, polyether ether ketone (PEEK), plastics, metals, bone grafts (allografts or autografts), synthetic bone analogs, thermoplastic resins, alloys, non-metals, and plastics, for example. The endplate 100 may be manufactured by any suitable technique, such as molding, casting, machining, three-dimensional printing, etching, and combinations thereof, for example.

The bone contact surfaces 122 are shown to be generally convexly shaped and to be aligned with one another so as to cooperate to provide a convexly shaped bone contact surface. However, it will be appreciated that the bone contact surfaces 122 may be formed to have any desired curvature, such as concave, substantially flat, irregular, and combinations thereof. Further, while the bone contact surfaces 122 are shown as being substantially smooth, in some exemplary embodiments one or more of a variety of bone engaging members may be implemented with the bone contact surfaces 122, such as teeth, spikes, roughened portions, bumps, grooves, knurls, striations, cavities, and combinations thereof, for example.

The bone contact surfaces 122 may be coated with various compounds to increase or limit bony on-growth or in-growth, promote healing, long term mobility, or allow for revision of the device, including hydroxyapatite, titanium-nickel, vapor plasma spray deposition of titanium, or plasma treatment to make the surface hydrophilic, and combinations thereof, for example. Also, a kit of endplates 100 having bone contact surfaces 122 with one or more varying sizes, shapes and angles may be provided.

The bone contact portion 104 may be oriented at varying angles relative to a plane perpendicular to a longitudinal axis of the endplate 100 to restore or approximate the approached spinal angulation, height, and curvature as will be appreciated by a person of ordinary skill in the art. The angle between the bone contact surfaces 122 and the plane may generally vary from about −10° to about 45°. As shown in FIG. 3, the orientation of the bone contact portion 104 may be varied by tapering the base portion 102 from one side to the other side in such a way that the dimensions of the annular channel 124 is also angled so that the flex characteristics of each of the bone contact sections 120 remains consistent. However, angularity may be affected in a number of different ways, such as changing the dimensions of the annular channel 124 or altering the dimensions of the bone contact sections 120. Typically, two or more endplates 100 having varying angles may be provided as a kit to allow surgeons to select the appropriate combination of endplates 100 to maintain the desired spinal alignment, height, angulation, or curvature, for example.

Referring now to FIGS. 5-8, another embodiment of an endplate 100*a* is shown connected to a support body 150. The endplate 100*a* is similar to the endplate 100 described above except that the endplate 100*a* and the support body 150 are configured to permit the angular orientation of the endplate 100*a* relative to the support body 150 to be adjusted.

The support body 150 may include a bearing plate 152, an elongated support member 154, a pin 156, and a locking member 158. The bearing plate 152 has a central opening 160 through which the pin 156 is disposed. An upper side of the bearing plate 152 has a recess 162 which is configured to pivotally mate with a corresponding portion of the endplate 100*a* as will be described below. A lower side of the bearing plate 152 may be formed to have a shaped and function similar to the base portion 102 of the endplate 100 described above. That is, the lower side of the bearing plate 152 may be adapted to be connected to the elongated support member 154. To this end, the lower side of the bearing plate 152 may include a connector 114*a*, e.g., a recess that is configured to receive and retain a corresponding portion of the elongated support member 154. The connector 114*a* may be formed in a variety of configurations for making connection with the elongated support member 154. For example, the bearing plate 152 may be attached to the elongated support member 154 by press fit or snap fit. Further, in some embodiments, bearing plate 152 and the elongated support member 154 may be formed as a unitary body.

The pin 156 has a head 166 which is shaped to pivotally mate with a portion of the endplate 100*a* in a manner to be discussed below.

The endplate 100*a* has a base portion 102*a* and a bone contact portion 104*a*. The base portion 102*a* is provided with a protrusion 168 extending from a lower end thereof and configured to pivotally mate with the recess 162. It will be appreciated that the positions of the protrusion and the recess may be interchanged so that the protrusion extends from the bearing plate 152 and the recess is formed in the base portion 102*a*.

The bone contact portion 104*a* may include a plurality of bone contact sections 120*a* with each of the bone contact sections 120*a* having a bone contact surface 122*a*. The bone contact sections 120*a* are constructed and function in a substantially similar manner to the bone contact sections 120 described above in reference to the endplate 100, except as noted below. In particular, the endplate 100*a* is further provided with a recess 170 in communication with a central opening 110*a*. The recess 170 is configured to pivotally mate with the head 166 of the pin 156.

The locking member 158 is adjustable between a locked condition wherein the pin 156 is caused to force the endplate 100*a* into frictional engagement with the bearing plate 152 to fix the angular orientation of the endplate 100*a* relative to the support body 150 and an unlocked condition wherein the pin 156 is caused to be in a relaxed condition so as to allow the endplate 100*a* to pivot relative to the support body 150 to allow the angulation of the endplate 100*a* to be altered to local patient anatomy and angulation, for example.

The locking member 158 may be implemented as any suitable locking member, such as a lock nut which is connected to the pin 156 so that axial movement of the lock nut causes the pin 156 of move axially between the locked condition and the unlocked condition. Desirably, the locking member 158 may be adjusted with a surgical tool (not shown) accessing the locking member 158 through an opening (not shown) formed in the elongated support member 154, although the adjustable locking member 158 may be adjusted in any suitable manner and from any suitable location, for example.

Figure 9:
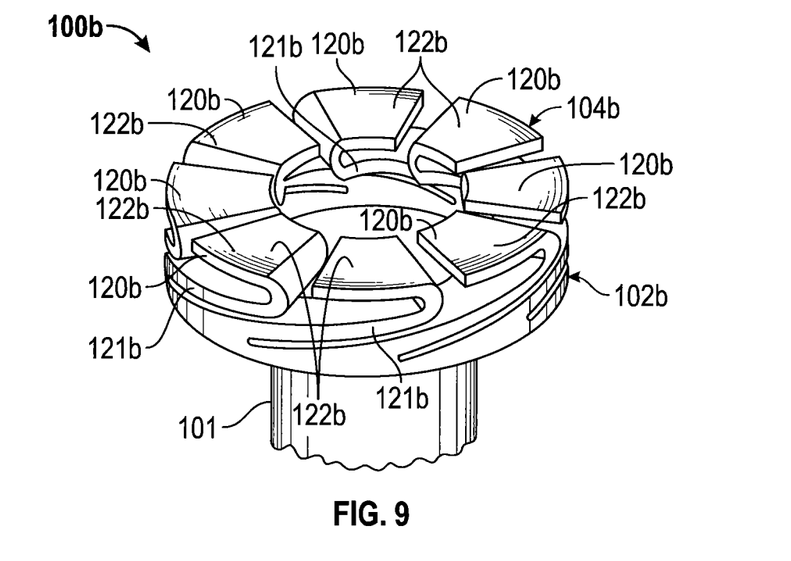
FIG. 9 is a perspective view of another embodiment of an endplate constructed in accordance with the inventive concepts disclosed herein shown connected to a portion of a support body.
Figure 10:
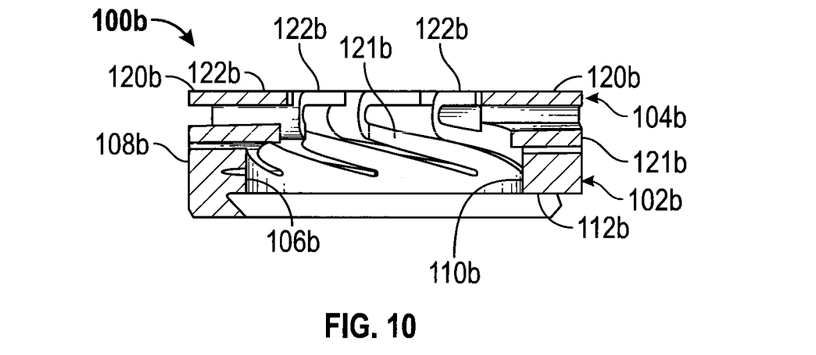
FIG. 10 is a cross-sectional view of the endplate of FIG. 19.

Referring now to FIGS. 9-10, another embodiment of an endplate 100*b* is shown. The endplate 100*b* is shown in FIG. 9 has being connected to a support body 101. The endplate 100*b* has a base portion 102*b* and a bone contact portion 104*b*. The base portion 102*b* provides a foundation for connecting with the support body 101 and for supporting the bone contact portion 104*b*. The bone contact portion 104*b* extends from the base portion 102 and is adapted to conform to the contour of the respective surface of a vertebral body with which the endplate 100*b* is positioned in contact to distribute loads placed on the endplate 100*b*.

As best illustrated in FIG. 10, the base portion 102*b* has an inner periphery 106*b* and an outer periphery 108*b* with the inner periphery 106*b* defining a central opening 110*b*. The base portion 102*b* is adapted to be connected to the support body 101. To this end, the base portion 102*b* may include a bottom surface 112*b* provided with a connector 114*b*, e.g., a notch that is configured to receive and retain a corresponding portion of the support body 101. The connector 114*b* may be formed in a variety of configurations for making connection with the central body 101. For example, the base portion 102*b* may be attached to the support body 101 by press fit or snap fit. Further, in some embodiments, the endplate 100 and the central body 101 may be formed as a unitary body, while in some exemplary embodiments the base portion 102*b* may be connected to the support body 101 via welds, seams, screws, brackets, bolts, joints, adhesives, and combinations thereof. In some exemplary embodiments of the inventive concepts disclosed herein, the support body 101 may be another bone contact portion 102*b* such that the vertebral implant includes a base portion 102*b* and two opposing bone-contacting portions 104*b*.

The bone contact portion 104*b* includes a plurality of bone contact sections 120*b* with each of the bone contact sections 120*b* having a bone contact surface 122*b*. The bone contact sections 120*b* extend from the base portion 102*b* in such a way that each of the bone contact sections 120*b* are sufficiently resilient so that the bone contact surfaces 122*b* are deflectable relative to the base portion 102*b* independently of the other the bone contact surfaces 122*b* when a compressive load is applied to the bone contact surfaces 122*b* of the bone contact sections 120*b*.

The bone contact sections 120*b* extend upwardly from the base portion 102*b* in a generally pinwheel pattern. Each of the bone contact sections 120*b* is illustrated as having a generally J-shaped configuration with a spring portion 121*b* that is dimensioned so that the bone contact surfaces 122*b* are resiliently deflectable. It should be appreciated that the spring portions 121*b* may be formed in a variety of shapes and sizes to affect the flexibility characteristics desired. The bone contact sections 120*b* are spaced from the adjacent bone contact sections 120*b* so that the bone contact sections 120*b* do not interfere with the deflection of the adjacent bone contact sections 120*b*.

In the exemplary embodiment shown in FIGS. 9 and 10, the bone contact portion 104*b* includes eight bone contact sections 120*b* which are of equal size and shape. However, the bone contact portion 104*b* may be formed to include a variety of different number of bone contact sections, such as two, three, four, five, six, seven, nine, or more. Further, the bone contact sections may be formed where the bone contact sections of the endplate 100*b* have different shapes and sizes, as well as different degrees of flexibility.

The endplate 100*b* may be formed to have a variety of shapes and sizes adapted to fit in the intervertebral space between adjacent vertebral bodies at any level of the spine. The endplate 100*b* may be constructed of any desired bio-inert, bio-active, or bio-absorbable implantable material, or combination of materials, including titanium, titanium alloys, surgical steel, nickel titanium (or nitinol), cobalt chromium, polyether ether ketone (PEEK), plastics, metals, bone grafts (allografts or autografts), synthetic bone analogs, thermoplastic resins, alloys, non-metals, and plastics, for example. The endplate 100 may be manufactured by any suitable technique, such as molding, casting, machining, three-dimensional printing, etching, and combinations thereof, for example.

The bone contact surfaces 122*b* may be coated with various compounds to increase or limit bony on-growth or in-growth, promote healing, long term mobility, or allow for revision of the device, including hydroxyapatite, titanium-nickel, vapor plasma spray deposition of titanium, or plasma treatment to make the surface hydrophilic, and combinations thereof, for example. Also, a kit of endplates 100*b* having bone contact surfaces 122*b* with one or more varying sizes, shapes and angles may be provided.

The endplate 100*b* may be implemented with the bone contact surfaces 122*b* having a fixed angular orientation or the endplate 100*b* may be implemented similarly to the endplate 100*a* such that the angular orientation of the endplate 100*b* is adjustable.

Figure 11:
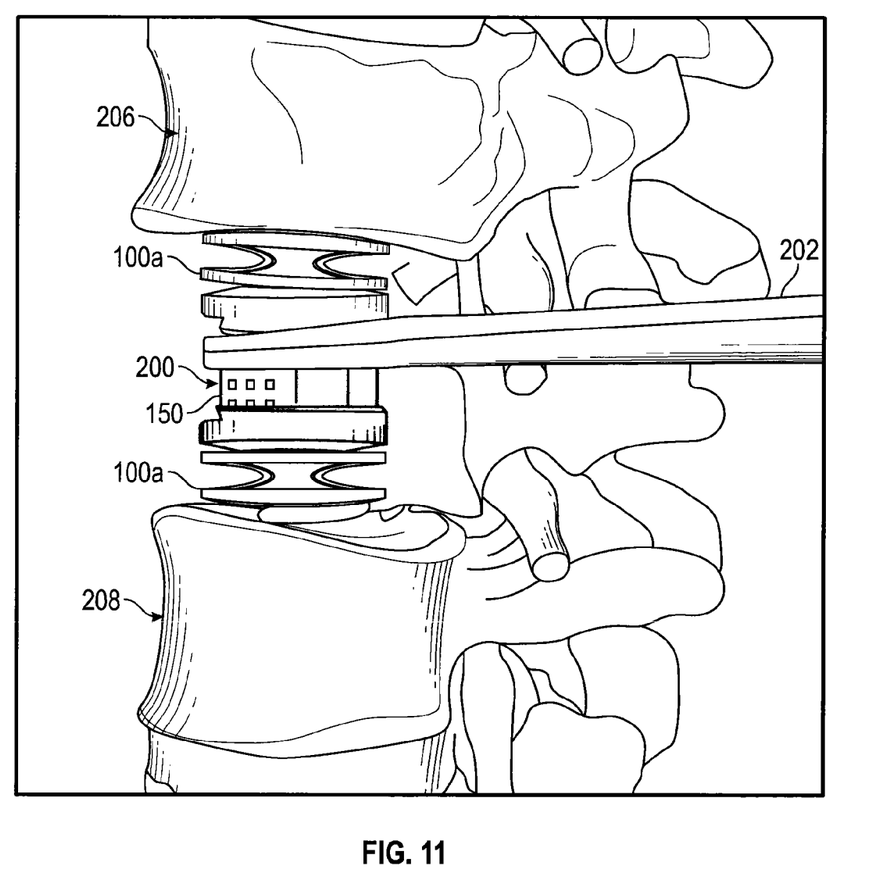
FIGS. 11 and 12 are diagrammatic views illustrating a procedure of implanting a vertebral implant into a patient.
Figure 12:
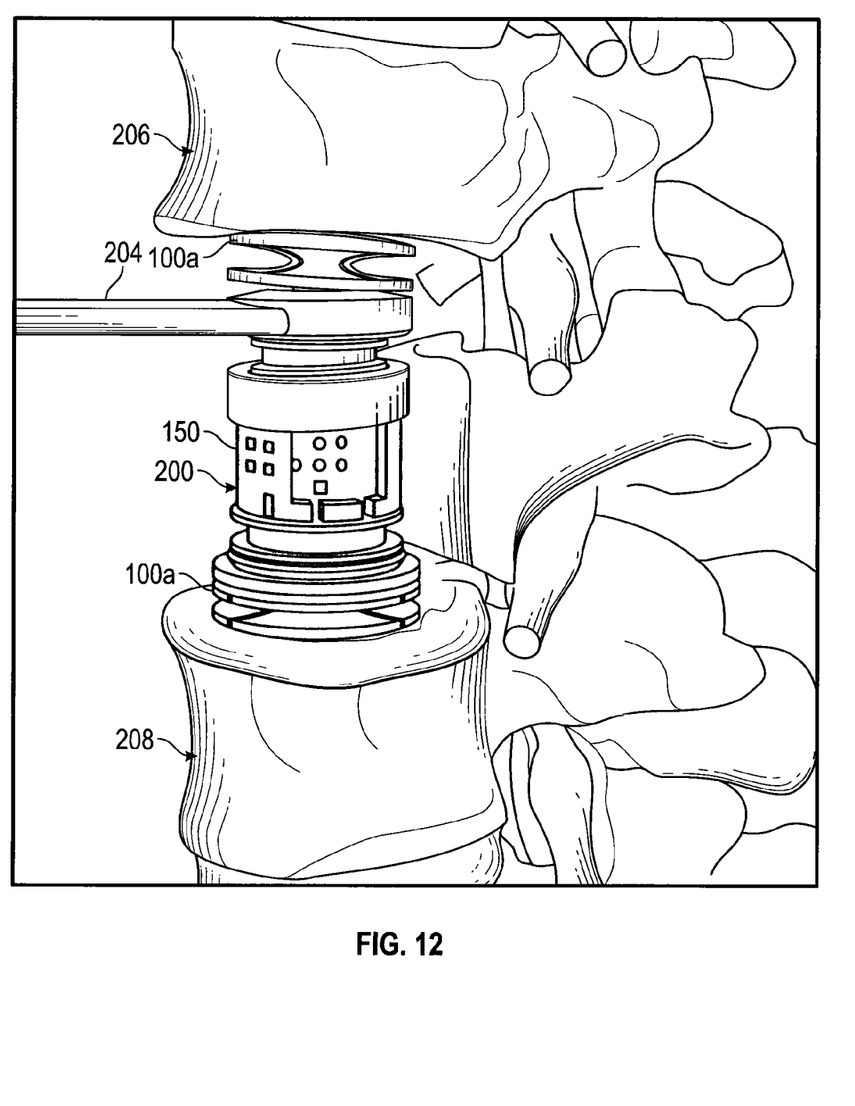

FIGS. 11 and 12 are diagrammatic views illustrating an exemplary VBR procedure of implanting a vertebral implant 200 that includes the endplate 100*a* described above. It is to be understood, however, that the procedure may be implemented for IBF procedures and with the endplate 100 and/or with the endplate 100*b* according to the inventive concepts disclosed herein, with some slight modifications, as will be readily appreciated by a person of ordinary skill in the art having the benefit of the instant disclosure.

The vertebral implant 200 is used by first removing the damaged vertebral body, along with the two adjacent intervertebral discs. The vertebral body surfaces of the two adjacent vertebrae 206 and 208 may be cleaned from debris, roughened, or otherwise prepared for receiving the vertebral implant 200.

One or two endplates 100*a* may be attached to the support body 150 of the vertebral implant. Alternatively, the endplate 100*a* may be supplied pre-attached to the device. The locking member 158 (FIG. 8) may be moved to the unlocked condition. The device along with the endplates 100*a* may be inserted into the location of the removed vertebral body and expanded to restore the desired spinal alignment, height, and curvature, for example. Any suitable surgical tool 202 may be used, which surgical tool 202 may be a generic surgical tool or may be specially designed for use with the vertebral body replace device 200, for example.

The angular orientation of the endplates 100*a* may be adjusted with the vertebral implant positioned between the vertebrae 206 and 208. A surgical tool 204 may be used to move the locking member 158 to the locked condition such that the angular orientation of the endplates 100*a* is secured.

A bone graft may be optionally added to the vertebral implant 200 such that the bone graft may grow through or around the vertebral implant 200 and fuse the vertebrae 206 and 208, for example.

It is to be understood that one or more endplate 100, one or more endplate 100*a*, one or more endplate 100*b*, or one or more existing endplates (not shown), and combinations thereof may be implemented with the inventive concepts disclosed therein to maintain or restore proper spinal alignment, height, or curvature, for example. For example, in some embodiments where an endplate 100 is implemented with the device 200, the implantation procedure may include selecting appropriate combinations of angles and sizes of one or more endplate 100 prior to implanting the device 200.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A vertebral implant, comprising: a support body; and an end plate pivotally connected to one end of the support body, the end plate comprising: a base portion connected to the support body; and a bone contact portion including a plurality of bone contact sections, each of the bone contact sections having a bone contact surface and extending from the base portion in such a way that each of the bone contact surfaces is deflectable relative to the base portion independently of an adjacent one of the bone contact surfaces when a compressive load is applied to the bone contact surfaces of the bone contact sections, wherein the end plate has a central opening with a recess formed near a proximal end of the bone contact sections, and wherein the support body comprises a pin extending through the central opening of the endplate, the pin having a head positioned in the recess of the end plate so as to allow the end plate to pivot relative to the pin.

2. The vertebral implant of claim 1, wherein the support body further has a bearing plate, and wherein the pin is positionable between a locked condition wherein the pin is caused to force the endplate into frictional engagement with the bearing plate of the support body to fix the angular orientation of the endplate relative to the support body and an unlocked position wherein the pin is caused to be in a relaxed condition so as to allow the endplate to pivot relative to the bearing plate.

3. The vertebral implant of claim 2, further comprising a locking nut connected to the pin in such a way that axial movement of the locking nut moves the pin between the locked condition and the unlocked condition.

4. The vertebral implant of claim 1, wherein the base portion has an inner periphery and an outer periphery, and wherein the bone contact sections extend radially outwardly from the inner periphery of the base portion.

5. The vertebral implant of claim 1, wherein each of the bone contact sections is spaced a distance apart from an adjacent one of the bone contact sections.

6. The vertebral implant of claim 1, wherein each of the contact sections has a proximal end and a distal end, and wherein each of the bone contact sections flares outwardly from the proximal end to the distal end.

\* \* \* \* \*